(12) United States Patent
Stivland et al.

(10) Patent No.: US 8,292,874 B2
(45) Date of Patent: Oct. 23, 2012

(54) CATHETER HAVING IMPROVED BONDING REGION

(75) Inventors: Timothy M. Stivland, Plymouth, MN (US); Elias A. Khoury, Champlin, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 126 days.

(21) Appl. No.: 12/907,593

(22) Filed: Oct. 19, 2010

(65) Prior Publication Data

US 2011/0034904 A1     Feb. 10, 2011

Related U.S. Application Data

(63) Continuation of application No. 11/379,534, filed on Apr. 20, 2006, now Pat. No. 7,815,625, which is a continuation of application No. 09/178,126, filed on Oct. 23, 1998, now abandoned.

(51) Int. Cl.
*A61M 25/00* (2006.01)

(52) U.S. Cl. ..................................................... 604/524

(58) Field of Classification Search ............... 604/96.01, 604/102.01, 102.02, 102.03, 103.04, 523, 604/524, 525, 526, 527
See application file for complete search history.

(56) References Cited

U.S. PATENT DOCUMENTS

| | | | |
|---|---|---|---|
| 2,687,131 A | 8/1954 | Raiche | |
| 2,936,760 A | 5/1960 | Gants | |
| 3,225,762 A | 12/1965 | Guttman | |
| 3,561,493 A | 2/1971 | Maillard et al. | |
| 3,618,614 A | 11/1971 | Flynn | |
| 3,695,921 A | 10/1972 | Shepherd et al. | |
| 3,814,137 A | 6/1974 | Martinez | |
| 3,884,242 A | 5/1975 | Bazell et al. | |
| 3,890,976 A | 6/1975 | Bazell et al. | |
| 4,044,765 A | 8/1977 | Kline | |
| 4,157,932 A | 6/1979 | Hirata | |
| 4,171,416 A | 10/1979 | Motegi et al. | |
| 4,211,741 A | 7/1980 | Ostoich | |
| 4,282,876 A | 8/1981 | Flynn | |
| 4,289,128 A | 9/1981 | Rusch | |

(Continued)

FOREIGN PATENT DOCUMENTS

CA      2078201 A1    12/1992

(Continued)

*Primary Examiner* — Nicholas Lucchesi
*Assistant Examiner* — Aarti B Berdichevsky
(74) *Attorney, Agent, or Firm* — Seager, Tufte & Wickhem LLC

(57) ABSTRACT

A catheter having a flexible outer tube and a lubricious inner tube bonded within the flexible outer tube. One catheter has a distal outer tube formed of a substantial portion of a first, flexible material, an inner tube having a lubricious inside wall surface formed of a second, lubricious material, and an outer tube wall surface compatible with heat bonding the inner tube outside wall surface to the outer tube wall surface. A preferred flexible material is polyether block amide (PEBA) and a preferred lubricious material is polyethylene. One catheter utilizing the invention includes a flexible distal outer tube having an orifice through the tube wall and an inner tube inserted through the orifice having a lubricious inner layer surrounded by a tie-layer, surrounded in turn by the same flexible material forming the outer tube. One catheter has a PEBA outer tube heat bonded to a tri-layer inner guide wire tube formed of a polyethylene inner layer, a PEBA outer layer, and a PLEXAR™ tie-layer disposed between the inner and outer layers.

11 Claims, 6 Drawing Sheets

U.S. PATENT DOCUMENTS

| | | |
|---|---|---|
| 4,323,071 A | 4/1982 | Simpson et al. |
| 4,335,723 A | 6/1982 | Patel |
| 4,413,989 A | 11/1983 | Schjeldahl et al. |
| 4,468,224 A | 8/1984 | Enzmann et al. |
| 4,596,563 A | 6/1986 | Pande |
| 4,597,755 A | 7/1986 | Samson et al. |
| 4,619,263 A | 10/1986 | Frisbie et al. |
| 4,627,844 A | 12/1986 | Schmitt |
| 4,636,346 A | 1/1987 | Gold et al. |
| 4,646,719 A | 3/1987 | Neuman et al. |
| 4,662,368 A | 5/1987 | Hussein et al. |
| 4,702,252 A | 10/1987 | Brooks et al. |
| 4,705,507 A | 11/1987 | Boyles |
| 4,707,389 A | 11/1987 | Ward |
| 4,719,924 A | 1/1988 | Crittenden et al. |
| 4,729,914 A | 3/1988 | Kliment et al. |
| 4,744,366 A | 5/1988 | Jang |
| 4,748,982 A | 6/1988 | Horzewski et al. |
| 4,762,129 A | 8/1988 | Bonzel |
| 4,763,654 A | 8/1988 | Jang |
| 4,769,099 A | 9/1988 | Therriault |
| 4,771,777 A | 9/1988 | Horzewski et al. |
| 4,775,371 A | 10/1988 | Mueller, Jr. |
| 4,776,849 A | 10/1988 | Shinno et al. |
| 4,782,834 A | 11/1988 | Maguire et al. |
| 4,798,598 A | 1/1989 | Bonello et al. |
| 4,820,349 A | 4/1989 | Saab |
| 4,824,435 A | 4/1989 | Giesy et al. |
| 4,838,268 A | 6/1989 | Keith et al. |
| 4,846,174 A | 7/1989 | Willard et al. |
| 4,863,449 A | 9/1989 | Therriault et al. |
| 4,877,031 A | 10/1989 | Conway et al. |
| 4,881,547 A | 11/1989 | Danforth |
| 4,896,670 A | 1/1990 | Crittenden |
| 4,898,591 A | 2/1990 | Jang et al. |
| 4,900,314 A | 2/1990 | Quackenbush |
| 4,906,241 A | 3/1990 | Noddin et al. |
| 4,906,244 A | 3/1990 | Pinchuk et al. |
| 4,917,088 A | 4/1990 | Crittenden |
| 4,921,478 A | 5/1990 | Solano et al. |
| 4,921,483 A | 5/1990 | Wijav et al. |
| 4,923,450 A | 5/1990 | Maeda et al. |
| 4,928,693 A | 5/1990 | Goodin et al. |
| 4,940,062 A | 7/1990 | Hampton et al. |
| 4,940,179 A | 7/1990 | Soni |
| 4,943,278 A | 7/1990 | Euteneuer et al. |
| 4,944,745 A | 7/1990 | Sogard et al. |
| 4,946,466 A | 8/1990 | Pinchuk et al. |
| 4,953,553 A | 9/1990 | Tremulis |
| 4,955,895 A | 9/1990 | Sugiyama et al. |
| 4,960,410 A | 10/1990 | Pinchuk |
| 4,976,690 A | 12/1990 | Solar et al. |
| 4,976,720 A | 12/1990 | Machold et al. |
| 4,981,478 A | 1/1991 | Evard et al. |
| 4,988,356 A | 1/1991 | Crittenden et al. |
| 4,994,018 A | 2/1991 | Saper |
| 4,994,032 A | 2/1991 | Sugiyama et al. |
| 4,994,047 A | 2/1991 | Walker et al. |
| 4,998,917 A | 3/1991 | Gaiser et al. |
| 4,998,923 A | 3/1991 | Samson et al. |
| 5,006,119 A | 4/1991 | Acker et al. |
| 5,026,377 A | 6/1991 | Burton et al. |
| 5,032,113 A | 7/1991 | Burns |
| 5,034,001 A | 7/1991 | Garrison et al. |
| 5,035,686 A | 7/1991 | Crittenden et al. |
| 5,035,694 A | 7/1991 | Kasprzyk et al. |
| 5,035,705 A | 7/1991 | Burns |
| 5,040,548 A | 8/1991 | Yock |
| 5,041,089 A | 8/1991 | Mueller et al. |
| 5,041,100 A | 8/1991 | Rowland et al. |
| 5,042,985 A | 8/1991 | Elliot et al. |
| 5,047,045 A | 9/1991 | Arney et al. |
| 5,050,606 A | 9/1991 | Tremulis |
| 5,057,120 A | 10/1991 | Farcot |
| 5,059,269 A | 10/1991 | Hu et al. |
| 5,061,273 A | 10/1991 | Yock |
| 5,063,018 A | 11/1991 | Fontirroche et al. |
| 5,078,727 A | 1/1992 | Hannam et al. |
| 5,085,649 A | 2/1992 | Flynn |
| 5,100,381 A | 3/1992 | Burns |
| 5,102,390 A | 4/1992 | Crittenden et al. |
| 5,102,403 A | 4/1992 | Alt |
| 5,112,304 A | 5/1992 | Barlow et al. |
| 5,114,423 A | 5/1992 | Kasprzyk et al. |
| 5,120,323 A | 6/1992 | Shockey et al. |
| 5,147,315 A | 9/1992 | Weber |
| 5,156,594 A | 10/1992 | Keith |
| 5,169,386 A | 12/1992 | Becker et al. |
| 5,176,637 A | 1/1993 | Sagae |
| 5,180,367 A | 1/1993 | Kontos et al. |
| 5,195,969 A | 3/1993 | Wang et al. |
| 5,195,971 A | 3/1993 | Sirhan |
| 5,209,729 A | 5/1993 | Hofmann et al. |
| 5,221,270 A | 6/1993 | Parker |
| 5,234,416 A | 8/1993 | Macauley et al. |
| 5,242,396 A | 9/1993 | Evard |
| 5,250,069 A | 10/1993 | Nobuyoshi et al. |
| 5,254,090 A | 10/1993 | Lombardi et al. |
| 5,267,959 A | 12/1993 | Forman |
| 5,270,086 A | 12/1993 | Hamlin |
| 5,272,012 A | 12/1993 | Opolski |
| 5,279,560 A | 1/1994 | Morrill et al. |
| 5,290,230 A | 3/1994 | Ainsworth et al. |
| 5,290,306 A | 3/1994 | Trotta et al. |
| 5,300,085 A | 4/1994 | Yock |
| 5,304,134 A | 4/1994 | Kraus et al. |
| 5,338,299 A | 8/1994 | Barlow |
| 5,346,505 A | 9/1994 | Leopold |
| 5,348,536 A | 9/1994 | Young et al. |
| 5,356,709 A | 10/1994 | Woo et al. |
| 5,383,853 A | 1/1995 | Jung et al. |
| 5,383,890 A | 1/1995 | Miraki et al. |
| 5,389,087 A | 2/1995 | Miraki |
| 5,395,332 A | 3/1995 | Ressemann et al. |
| 5,397,306 A | 3/1995 | Nobuyoshi et al. |
| 5,403,292 A | 4/1995 | Ju |
| 5,405,338 A | 4/1995 | Kranys |
| 5,409,495 A | 4/1995 | Osborn |
| 5,423,754 A | 6/1995 | Cornelius et al. |
| 5,425,711 A | 6/1995 | Ressemann et al. |
| 5,425,712 A | 6/1995 | Goodin |
| 5,439,454 A | 8/1995 | Lo et al. |
| 5,449,343 A | 9/1995 | Samson et al. |
| 5,449,372 A * | 9/1995 | Schmaltz et al. ............ 606/198 |
| 5,454,795 A | 10/1995 | Samson |
| 5,460,608 A | 10/1995 | Lodin et al. |
| 5,478,320 A | 12/1995 | Trotta |
| 5,484,444 A | 1/1996 | Braunschweiler et al. |
| 5,490,837 A | 2/1996 | Blaeser et al. |
| 5,496,275 A | 3/1996 | Sirhan et al. |
| 5,496,294 A | 3/1996 | Hergenrother et al. |
| 5,499,973 A | 3/1996 | Saab |
| 5,501,759 A | 3/1996 | Forman |
| 5,514,236 A | 5/1996 | Avellant et al. |
| 5,520,647 A | 5/1996 | Solar |
| 5,527,281 A | 6/1996 | Haas |
| 5,533,985 A | 7/1996 | Wang |
| 5,538,510 A | 7/1996 | Fontirroche et al. |
| 5,545,151 A * | 8/1996 | O'Connor et al. ............ 604/524 |
| 5,549,552 A | 8/1996 | Peters et al. |
| 5,558,737 A | 9/1996 | Brown et al. |
| 5,562,127 A | 10/1996 | Fanselow et al. |
| 5,571,087 A | 11/1996 | Ressemann et al. |
| 5,584,821 A | 12/1996 | Hobbs et al. |
| 5,587,125 A | 12/1996 | Roychowdhury |
| 5,599,325 A * | 2/1997 | Ju et al. ........................ 604/524 |
| 5,620,649 A | 4/1997 | Trotta |
| 5,643,209 A | 7/1997 | Fugoso et al. |
| 5,645,533 A | 7/1997 | Blaeser et al. |
| 5,653,691 A | 8/1997 | Rupp et al. |
| 5,676,659 A | 10/1997 | McGurk |
| 5,695,468 A | 12/1997 | Lafontaine et al. |
| 5,702,439 A | 12/1997 | Keith et al. |
| 5,720,724 A | 2/1998 | Ressemann et al. |
| 5,728,063 A | 3/1998 | Preissman et al. |
| 5,728,067 A | 3/1998 | Enger |
| 5,728,088 A | 3/1998 | Magruder et al. |

| | | | | | | |
|---|---|---|---|---|---|---|
| 5,733,400 | A | 3/1998 | Gore et al. | EP | 0344530 A1 | 12/1989 |
| 5,743,875 | A | 4/1998 | Sirhan et al. | EP | 0351687 A2 | 1/1990 |
| 5,749,852 | A | 5/1998 | Schwab et al. | EP | 0358117 B1 | 3/1990 |
| 5,792,116 | A | 8/1998 | Berg et al. | EP | 0365993 A1 | 5/1990 |
| 5,792,814 | A | 8/1998 | Oishi et al. | EP | 0368523 A2 | 5/1990 |
| 5,797,877 | A | 8/1998 | Hamilton et al. | EP | 0380873 B1 | 5/1990 |
| 5,820,594 | A | 10/1998 | Fontirroche et al. | EP | 0380102 A1 | 8/1990 |
| 5,824,173 | A | 10/1998 | Fontirroche et al. | EP | 0380873 A2 | 8/1990 |
| 5,833,706 | A | 11/1998 | St. Germain et al. | EP | 0380873 A3 | 8/1990 |
| 5,837,313 | A | 11/1998 | Ding et al. | EP | 0405831 A2 | 1/1991 |
| 5,843,032 | A | 12/1998 | Kastenhofer | EP | 0420488 A1 | 4/1991 |
| 5,876,344 | A | 3/1999 | Baker et al. | EP | 0436501 B1 | 7/1991 |
| 5,904,670 | A | 5/1999 | Schrainer | EP | 0452123 A1 | 10/1991 |
| 5,964,778 | A | 10/1999 | Fugoso et al. | EP | 0456342 A1 | 11/1991 |
| 5,968,009 | A | 10/1999 | Siman | EP | 0520692 A1 | 12/1992 |
| 6,102,890 | A * | 8/2000 | Stivland et al. ............ 604/96.01 | EP | 0530201 B1 | 3/1993 |
| 6,299,595 | B1 | 10/2001 | Dutta et al. | EP | 0650740 A1 | 5/1995 |
| 6,387,075 | B1 * | 5/2002 | Stivland et al. ............ 604/96.01 | EP | 0669142 A2 | 8/1995 |
| 6,520,951 | B1 | 2/2003 | Carrillo, Jr. et al. | EP | 0707865 A1 | 4/1996 |
| 6,547,768 | B2 | 4/2003 | Trotta | EP | 0803264 A1 | 10/1997 |
| 6,589,226 | B1 | 7/2003 | Owens | EP | 0821981 B1 | 2/1998 |
| 6,610,068 | B1 | 8/2003 | Yang | EP | 0920883 A1 | 6/1999 |
| 6,613,075 | B1 | 9/2003 | Healy et al. | EP | 1084728 A1 | 3/2001 |
| 6,635,029 | B1 | 10/2003 | Venturelli | GB | 2130093 A | 5/1984 |
| 6,712,807 | B2 * | 3/2004 | Stivland et al. ............... 604/524 | GB | 2209121 A | 5/1989 |
| 6,746,423 | B1 | 6/2004 | Wantink | JP | 9084871 A2 | 3/1997 |
| 6,887,219 | B2 | 5/2005 | Wantink | SU | 627828 A1 | 10/1978 |
| 6,890,318 | B2 | 5/2005 | Wantink | SU | 1251914 A | 8/1986 |
| 6,893,417 | B2 | 5/2005 | Gribbons et al. | WO | 8902763 A1 | 4/1989 |
| 6,923,787 | B2 | 8/2005 | Wang | WO | 9211893 A1 | 7/1992 |
| 6,997,908 | B2 | 2/2006 | Carrillo, Jr. et al. | WO | 9305841 A1 | 4/1993 |
| 7,022,104 | B2 | 4/2006 | Konstantino | WO | 9305842 A1 | 4/1993 |
| 7,048,713 | B2 | 5/2006 | Wang | WO | 9402194 A1 | 2/1994 |
| 2004/0054323 | A1 | 3/2004 | Wantink | WO | 9509667 A1 | 4/1995 |
| | | | | WO | 9518647 A2 | 7/1995 |
| | | FOREIGN PATENT DOCUMENTS | | WO | 9528982 A1 | 11/1995 |
| EP | | 0161863 A2 | 11/1985 | WO | 9600099 A1 | 1/1996 |
| EP | | 0277368 A1 | 8/1988 | WO | 9620752 A1 | 7/1996 |
| EP | | 0279959 B1 | 8/1988 | WO | 9726027 A1 | 7/1997 |
| EP | | 0298634 A1 | 8/1988 | | | |

\* cited by examiner

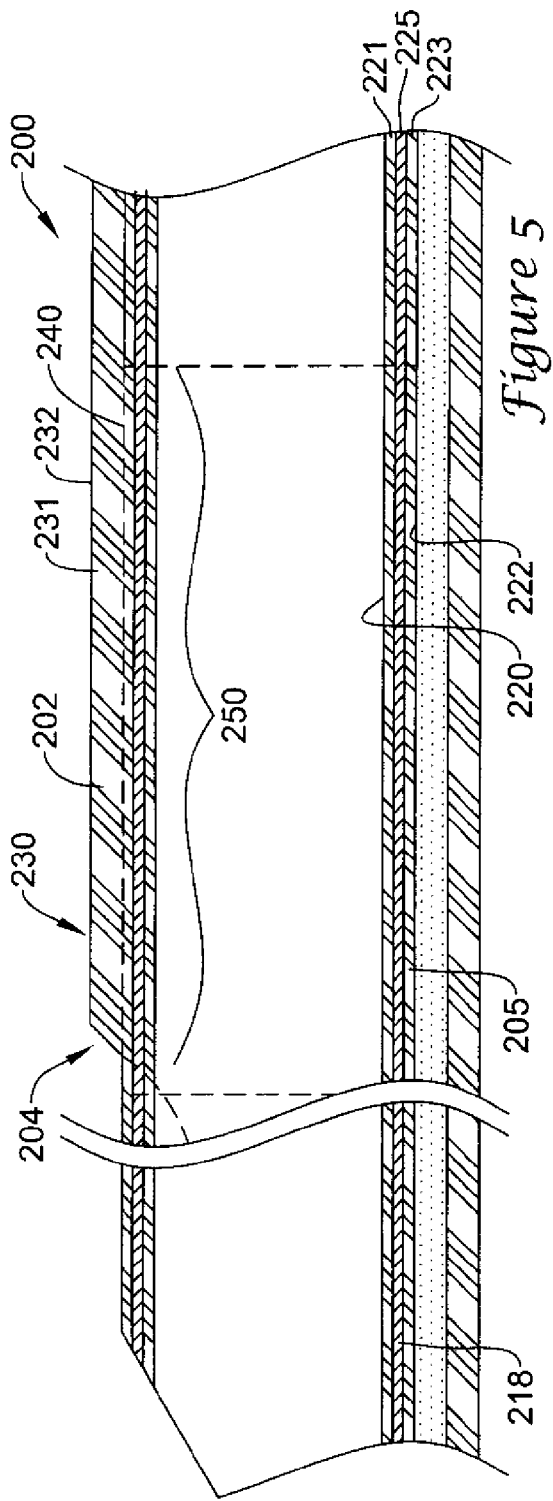
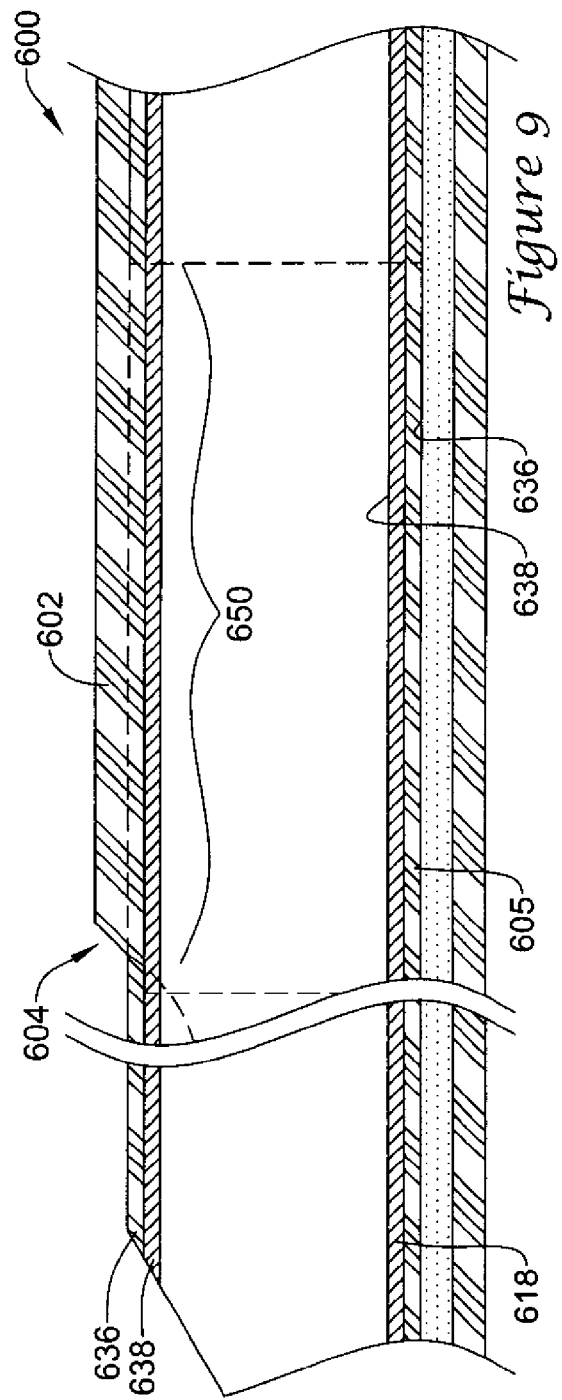

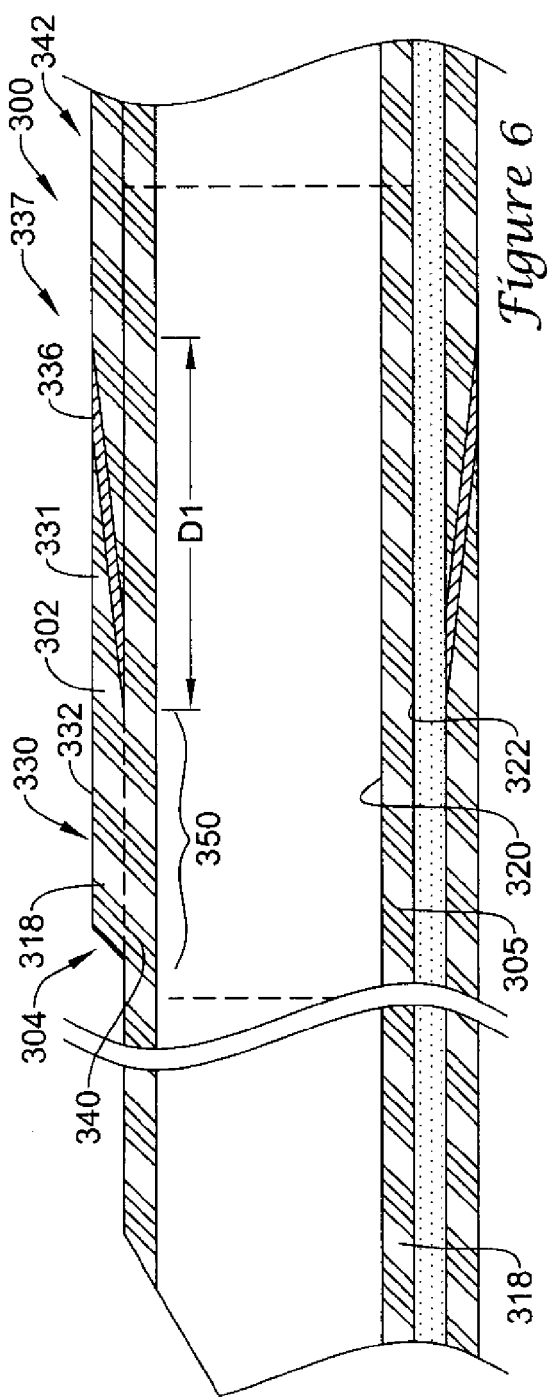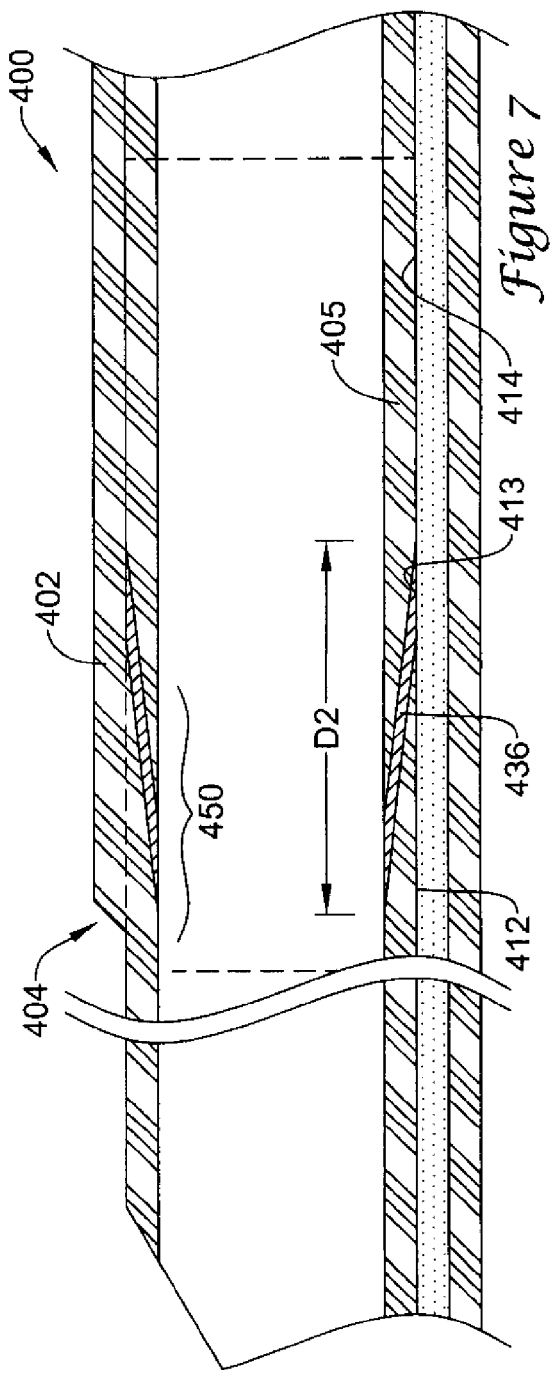

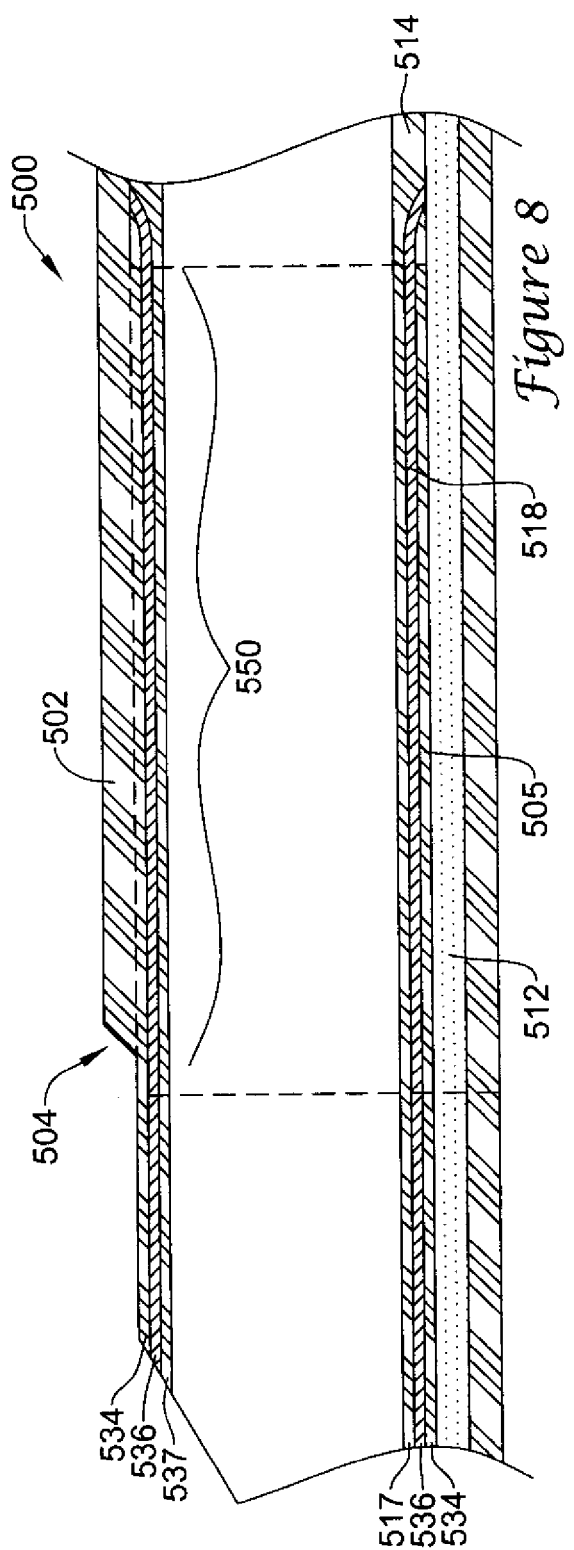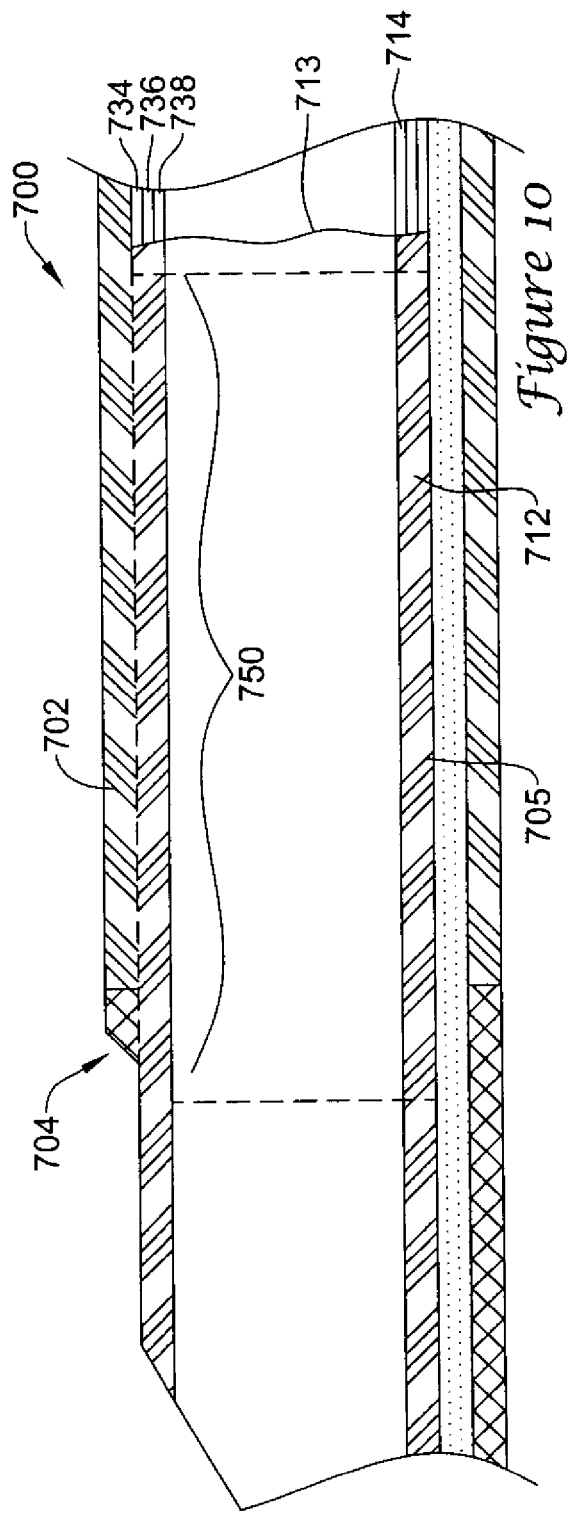

CATHETER HAVING IMPROVED BONDING REGION

RELATED APPLICATIONS

This application is a continuation application of U.S. application Ser. No. 11/379,534 filed Apr. 20, 2006, now U.S. Pat. No. 7,815,625, which is a continuation application of U.S. application Ser. No. 09/178,126 filed Oct. 23, 1998.

FIELD OF THE INVENTION

The present invention relates generally to medical devices. More specifically, the present invention relates to angioplasty catheters. In particular, the present invention includes angioplasty catheters having distal, short, lubricious inner guide wire tubes bonded within flexible outer tubes.

BACKGROUND OF THE INVENTION

Angioplasty procedures have gained wide acceptance in recent years as efficient and effective methods for treating types of vascular disease. In particular, angioplasty is widely used for opening stenoses in the coronary arteries and is used for treating stenoses in other vascular regions.

One widely used form of angioplasty makes use of a dilatation catheter which has a inflatable balloon at the distal end and a guide wire lumen within at least a portion of the catheter shaft. Typically, a guide wire is inserted through the vascular system to a position near the stenoses, leaving a proximal portion of the guide wire extending from the patient. The proximal guide wire portion is threaded through the dilatation catheter guide wire lumen, and the dilatation catheter is advanced through the vascular system over the guide wire to a position near the stenoses. The treating physician manipulates the dilatation catheter until the balloon is positioned across the stenoses. The balloon is then inflated by supplying fluid under pressure through an inflation lumen in the catheter to the balloon. The inflation of the balloon widens the vessel lumen through the stenosed area by pressing the inflating balloon wall against the lesion inside wall.

One class of dilatation catheters, termed "Single Operator Exchange" (SOE) or "Rapid Exchange" catheters, have only a short, distal guide wire lumen, to allow for easy removal and replacement of catheters while requiring only a short length of guide wire extending proximally from a patient. These catheters include a distal portion having multiple desired attributes. The catheter distal portion preferably has a small profile or cross-sectional area and is very flexible, to allow for traversing narrow and tortuous vessel paths. The distal portion may also require a guide wire tube having a lumen, which increases the profile. The guide wire lumen preferably has a lubricious inside wall to ease movement of the catheter over the guide wire.

Many current SOE catheters have outer polyethylene tubes and inner polyethylene guide wire tubes inserted therein. An orifice can be created in the side of the outer tube wall and the inner tube inserted through the orifice. The inner tube is inserted so as to extend longitudinally through the lumen of the outer tube. On one side of the inner tube, distal of the orifice, the outside surface of the inner tube runs close to the inside surface of the outer tube. On the opposite direction, proximal of the orifice, the outside surface of the inner tube runs along the outside surface of the outer tube, in a crimped or buckled hollow surface region. The close proximity of the tube surfaces suggests bonding using adhesive or heat bonding. Heat bonding is preferred to adhesive bonding.

Polyether block amide (PEBA) tubes have greater flexibility than polyethylene tubes, and it would be desirable to use PEBA tubes for the outer tubes. It is very desirable to have the inner and outer tubes formed of mutually compatible materials to enable heat bonding. Use of PEBA for guide wire inner tubes would provide such heat bonding compatibility. PEBA is generally less lubricious than polyethylene, however, making polyethylene a more desirable material for forming the inner tube. Lubricity is important for providing a low friction inner surface for accepting a guide wire. What would be desirable is a catheter allowing for use of a more flexible outer tube while retaining the benefits of a more lubricious inner tube while allowing high-quality heat bonding between the two tubes.

SUMMARY OF THE INVENTION

The present invention includes catheters having a first tube formed primarily of a first material bonded to a second tube having an inside surface formed primarily of a second material, where the first and second materials may be unsuited for high quality direct bonding. One catheter has a first tube formed of a flexible material such as polyether block amide and a second, tri-layer tube having a lubricious inside layer such as polyethylene, a flexible outside layer formed of the same material as the first tube outside surface, and an intermediate tie-layer suitable for joining the lubricious and flexible layers. In a preferred embodiment, the first tube has an orifice through a wall and the second tube is inserted through the wall and distally disposed within the first, outer tube. In a preferred embodiment, the first tube functions as a distal catheter shaft and the second tube functions as a short, distal guide wire tube disposed within, and bonded to, the first tube.

Catheters incorporating the invention include single operator exchange (SOE) angioplasty balloon catheters having a proximal shaft, a distal shaft including a first tube coupled to the proximal shaft, distally disposed inflatable balloon, and an orifice through the wall of the first tube disposed proximal of the balloon. In these catheters, a second guide wire tube can be inserted through the orifice and disposed distally of the orifice, commonly extending through the balloon region and ending in a distal guide wire port near the distal end of the catheter. The SOE catheters preferably have a lubricious material forming the inside layer of the inner tube and a flexible material forming most of the outer tube. A preferred lubricious material is polyethylene (PE) and a preferred flexible material is polyether block amide (PEBA).

One SOE catheter has a polyethylene inner tube disposed within a tri-layer outer tube having an inside PE layer, an outer PEBA layer, and a PLEXAR™ tie-layer disposed therebetween. The outer tube inside surface can be bonded to the inner tube outside surface. Another SOE catheter has a PE inner tube disposed within an interrupted tri-layer outer tube having a proximal PE portion, a distal PEBA portion, and a tie-layer interrupting the PE and PEBA portions. The inner tube outside surface can be bonded to the outer tube PE portion inside and outside surfaces. Another SOE catheter has a PEBA outer tube and an interrupted tri-layer inner tube disposed therein having a proximal PEBA portion, a distal PE portion, and a tie-layer disposed therebetween. The inner tube PEBA portion can be bonded to the outer tube PEBA inside and outside surfaces. Another SOE catheter includes a PEBA outer tube and a PE inner tube having a proximal tri-layer portion having a tie-layer disposed over the inside PE layer and a PEBA layer disposed over the tie-layer. The inner tube proximal portion outside PEBA surface can be bonded to the outer tube PEBA inside and outside surfaces.

Yet another SOE catheter includes a PEBA outer tube and a tri-layer inner tube having a PE inside layer, a PEBA outside layer, and a tie-layer disposed therebetween. The inner tube outside PEBA surface can be bonded to the outer tube PEBA inside and outside surfaces. In still another SOE catheter, an outer PEBA tube has a bi-layer inner tube disposed within including an inside high density PE (HDPE) layer and a PLEXAR™ tie-layer disposed over the HDPE inside layer. The inner tube outside tie-layer can be bonded to the outer tube PEBA inside surface. In one more embodiment, an SOE catheter includes a PEBA outer tube and an inner tube having a proximal PEBA portion butt-welded to a distal tri-layer portion having a PE inside layer, a PEBA outside layer, and a tie-layer disposed therebetween.

The present invention can provide catheters having the advantages of a lubricious guide wire tube, a flexible catheter shaft, and a secure bond between the lubricious material and the flexible material. Catheters according to the present invention can provide the advantages of both materials as well as providing the advantages of heat bonding the two materials.

BRIEF DESCRIPTION OF THE DRAWINGS

FIG. 5 is a longitudinal, cross-sectional view of a tri-layer inner guide wire tube inserted within and bonded to an outer tube, wherein the inner tube has an outside surface compatible with the inside surface of the outer tube;

FIG. 6 is a longitudinal, cross-sectional view of an inner guide wire tube inserted within and bonded to an interrupted tri-layer outer tube, wherein the outer tube has a proximal portion inside surface compatible with the outside surface of the inner tube, an intermediate portion tie-layer, and a distal portion having different properties than the proximal portion;

FIG. 7 is a longitudinal, cross-sectional view of an interrupted tri-layer inner guide wire tube inserted within and bonded to an outer tube, wherein the inner tube has a proximal portion outside surface compatible with the inside surface of the outer tube, an intermediate portion tie-layer, and a distal portion having different properties than the proximal portion;

FIG. 8 is a longitudinal, cross-sectional view of an inner guide wire tube inserted within and bonded to an outer tube, wherein the inner tube has a short, proximal tri-layer portion having an outside surface compatible with the inside surface of the outer tube and a distal portion having an outside surface corresponding to the inside layer of the tri-layer portion;

FIG. 9 a longitudinal, cross-sectional view of a bi-layer inner guide wire tube inserted within and bonded to an outer tube, wherein the inner tube has an outside tie-layer compatible with the inside surface of the outer tube; and FIG. 10 is a longitudinal, cross-sectional view of an inner guide wire tube inserted within and bonded to an outer tube, wherein the inner tube has a proximal portion having an outside surface compatible with the inside surface of the outer tube and a distal portion having different properties than the proximal portion butt-welded to the proximal portion.

DETAILED DESCRIPTION OF THE PREFERRED EMBODIMENTS

Figure 1:
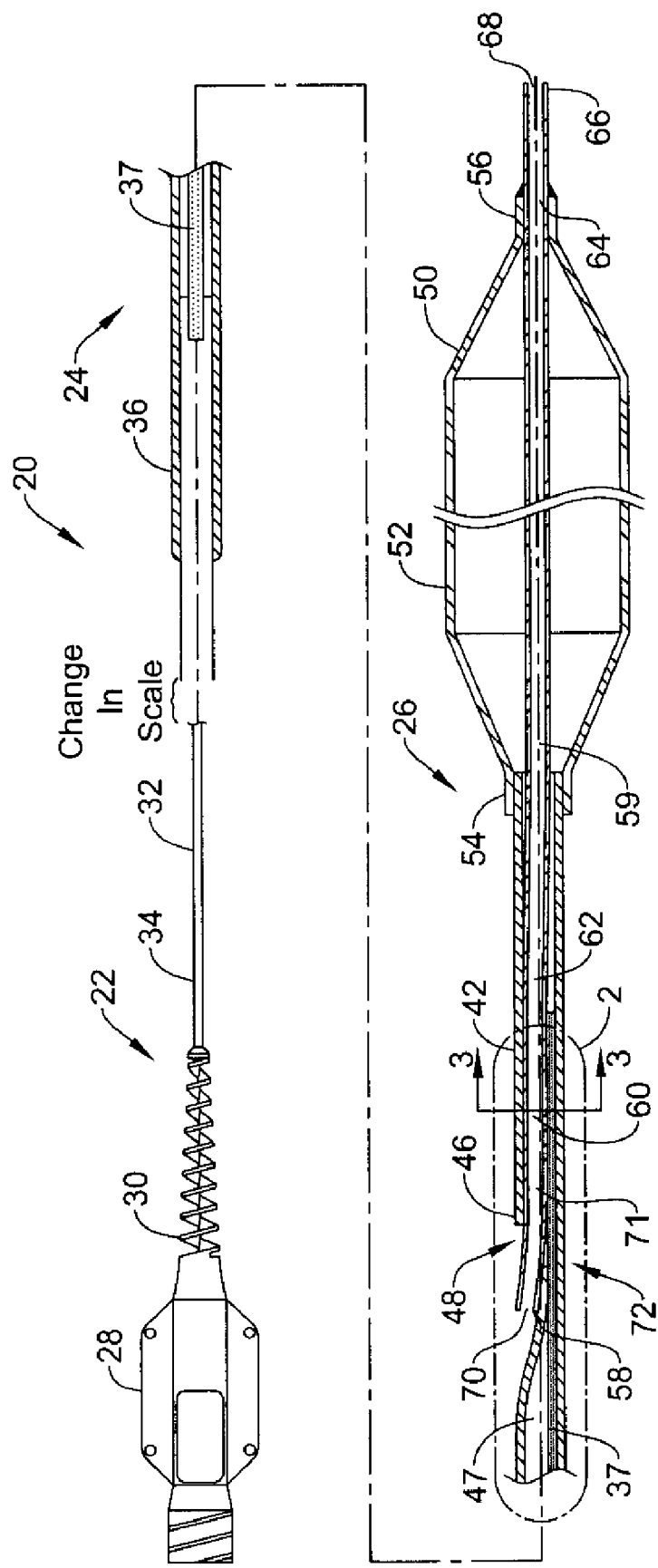
FIG. 1 is a longitudinal, cross-sectional view of a balloon angioplasty catheter including an inner guide wire tube inserted through an orifice in an outer tube and disposed within the outer tube.

FIG. 1 illustrates a balloon angioplasty catheter 20, which demonstrates one catheter incorporating the present invention. Catheter 20 extends from a proximal region 22 through an intermediate region 24 to a distal region 26. Proximal region 22 includes a manifold 28, a strain relief 30, and a proximal shaft 32. Proximal shaft 32 includes a proximal region 34 having an outer hypotube construction and a distal region 36 having a polymeric construction, continuing distally after the hypotube terminates. The term "hypotube," as used herein, refers generally to a thin walled, high-strength metallic tube having a lumen within. The hypotube is preferably a stainless steel hypodermic tube. In one embodiment, a core wire or stiffener 37 can be included in proximal region 22 and intermediate region 24 to provide additional stiffness and pushability to catheter 20 to enable pushing the catheter distal portion into distant body regions without buckling.

A distal shaft 42 includes an outer tube 46 and an orifice 48 through the outer wall of outer tube 46 and a lumen 47 within. A balloon 50 is disposed distally on distal shaft 42, having an envelope 52, a proximal waist 54, and a distal waist 56. An inner tube 58 is inserted into outer tube 46 and lumen 47 through orifice 48. Inner tube 58 serves as a distal guide wire tube in catheter 20. The relatively short length of inner tube 58 allows the single operator or rapid exchange of catheter 20 over a guide wire. Inner tube 58 includes a proximal orifice 70, a proximal end 71, a proximal portion 60, an intermediate portion 62, a distal portion 64, a distal end 66, a distal orifice 68, and a guide wire lumen 59 within. In use, a guide wire (not requiring illustration) can be threaded through proximal orifice 70, through lumen 59, exiting through distal orifice 68. Inner tube 58 is preferably substantially congruent within outer tube 46 for much of the length of inner tube 58. The entry of inner tube 58 through orifice 48 can include a buckled or concave region 72, also illustrated in FIG. 2 at 806. In this buckled region, inner tube 58 can lie atop outer tube 46 proximal of entry orifice 48. The entry of inner tube 58 into outer tube 46 preferably includes bonding or affixing of the tubes to secure inner tube 58 in place. This bonding preferably includes bonding in the region proximate orifice 48 and can include bonding both proximal and distal of orifice 48.

Figure 2:
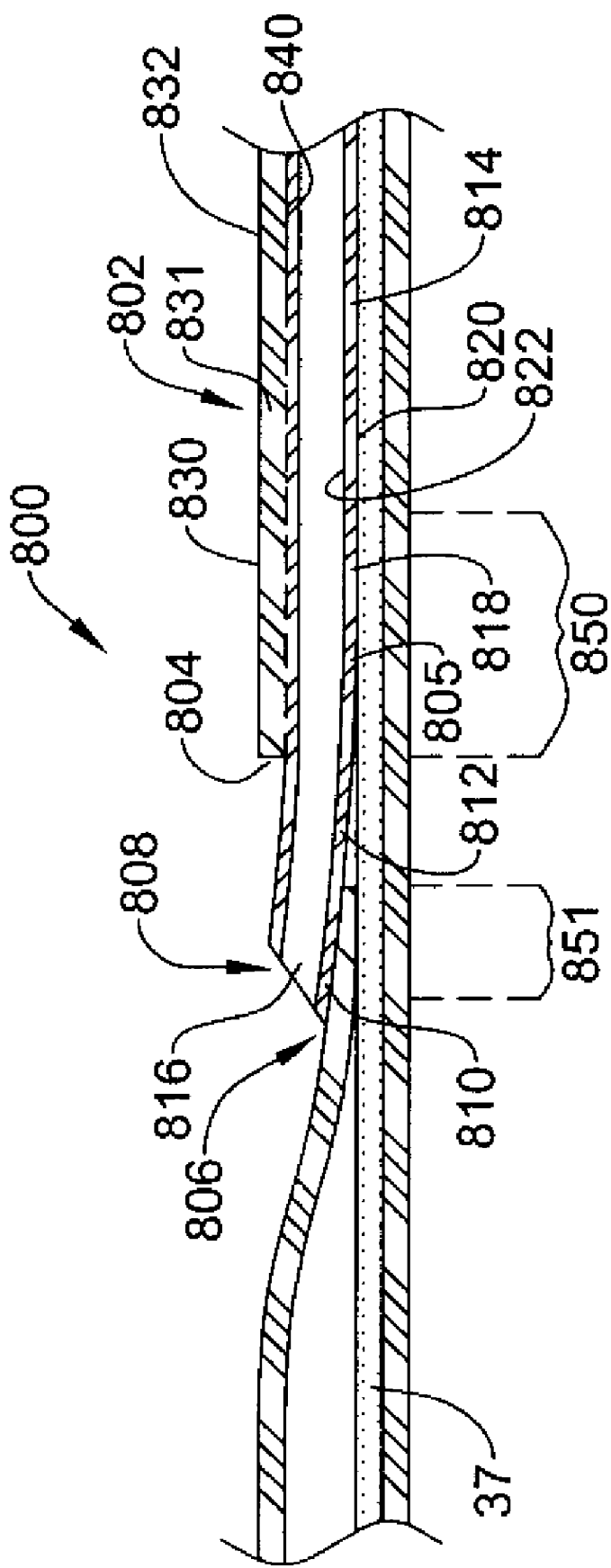
FIG. 2 is a fragmentary, longitudinal cross-sectional view of a distal portion of the catheter of FIG. 1, illustrating an inner tube extending through an orifice in an outer tube.

Referring now to FIG. 2, the region proximate the entry of the inner tube into the outer tube is illustrated in greater detail. The embodiments illustrated in FIGS. 4-10 can share many of the structural features of the embodiment of FIG. 2, while having different tube construction and bonding. FIG. 2 illustrates a catheter distal region 800 including an outer tube 802 having an orifice 804 therein and an inner guide wire tube 805 inserted distally though orifice 804. An orifice such as orifice 804 can be formed by making a slit or removing material and creating a hole in the outer tube wall. The orifice can serve to admit the inner tube into the outer tube. Inner tube 805 includes a proximal end 810, a proximal portion 812, a proximal orifice 808, and a guide wire lumen 816 through inner tube 805. Inner tube 805 lies in a buckled or concave region 806 in outer tube 802 proximal of where inner tube proximal portion 812 extends into outer tube 802. In one embodiment, the bonding region lies generally proximate orifice 804, which can be used for bonding of inner tube 805 to outer tube 802. Inner tube 805 includes an inner tube wall 818, an inside wall surface 822, and an outside wall surface 820. Inner tube 805 includes a distal portion 814, which lies distal of proximal portion 812. Outer tube 802 includes a proximal portion 830, a tube wall 831, an outside wall surface 832, and an inside surface 840.

In one embodiment, inner tube wall 818 is formed of a lubricious material to provide a lubricious inside surface 822 offering less resistance when advancing the catheter over a guide wire. In this embodiment, outer tube wall 831 is formed of the same or compatible lubricious material as inner tube 805. This allows bonding between inner and outer tubes as indicated, for example, at region 850. In some embodiments, bonding occurs distal of orifice 804 and near orifice 804. In other embodiments, the bonding occurs further distal of orifice 804. In other embodiments, bonding occurs proximal of orifice 804 as indicated, for example, by region 851. Any suitable location for bonding inner to outer tubes is within the scope of the invention.

Figure 3:
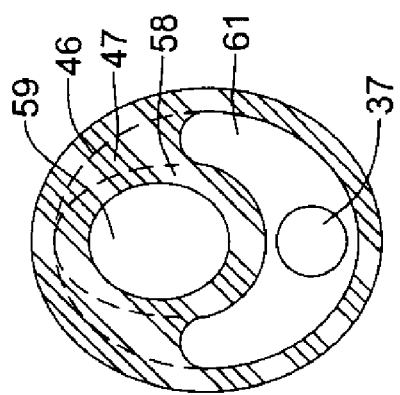
FIG. 3 is a transverse, cross-sectional view taken through 3-3 in FIG. 1, illustrating an outer tube, an inner tube, and a core wire.

Referring now to FIG. 3, a transverse cross section taken through 3-3 in FIG. 1 is further illustrated. Outer tube 46 has been heat bonded to inner tube 58, resulting in an area of melted polymer 47 between the inner and outer tubes. Guide wire lumen 59 is illustrated, together with core wire 37 and an inflation lumen 61. In one method, after the inner tube is positioned within the outer tube, mandrels corresponding to the guide wire and inflation lumens are positioned within the inner and outer tubes respectively. The tubular assembly is heated, resulting in a re-melt or re-flow of polymeric material and heat bonding.

Figure 4:
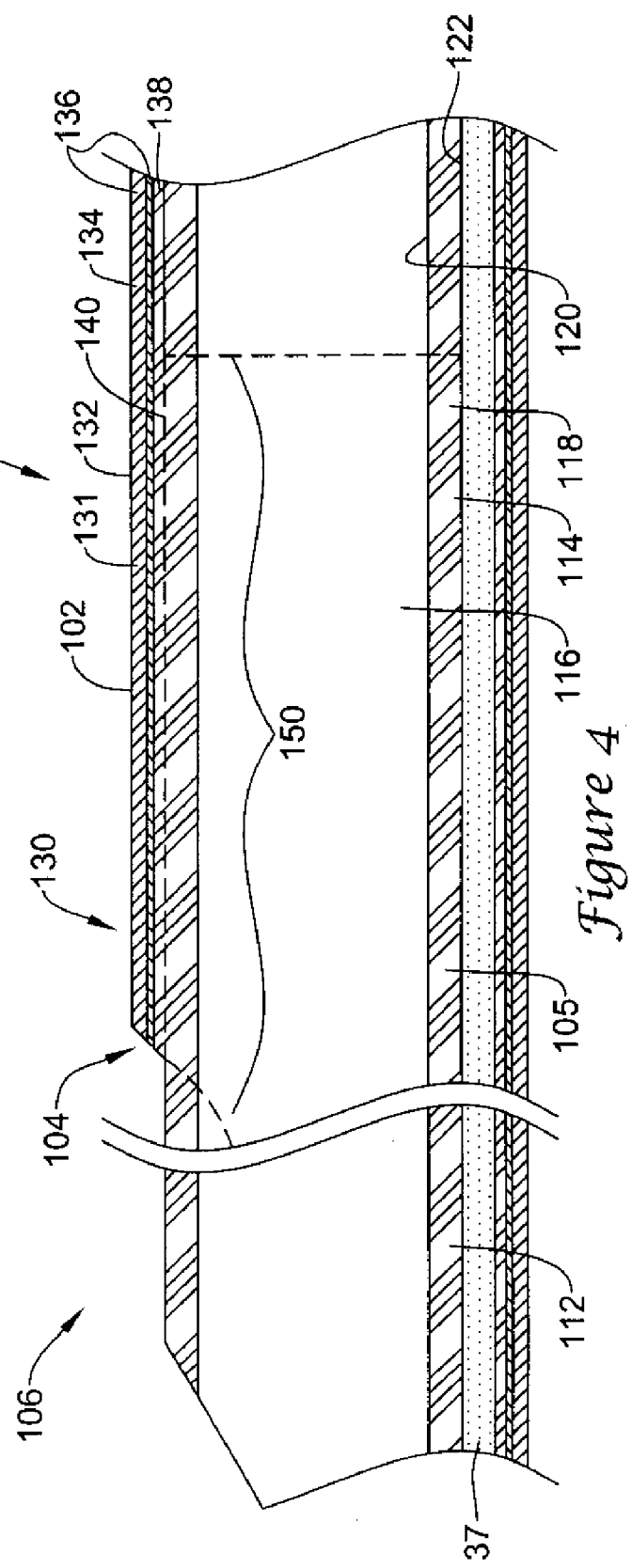
FIG. 4 is a longitudinal, cross-sectional view of an inner guide wire tube inserted within and bonded to a tri-layer outer tube, wherein the outer tube has an inside surface compatible with the outside surface of the inner tube.

Referring now to FIG. 4, a catheter distal region 100 is illustrated, including an outer tube 102 having an orifice 104 therein, and an inner guide wire tube 105 inserted distally though orifice 104. Inner tube 105 includes a proximal portion 112 and a guide wire lumen 116 through inner tube 105. Inner tube 105 lies in a buckled or concave region 106 in outer tube 102 proximal of where inner tube proximal portion 112 extends into outer tube 102. In one embodiment, the bonding region lies generally proximate orifice 104, which can be used for bonding of inner tube 105 to outer tube 102. Inner tube 105 includes an inner tube wall 118, an inside wall surface 120, and an outside wall surface 122. Inner tube 105 includes a distal portion 114, which lies distal of proximal portion 112. Outer tube 102 includes a proximal portion 130, a tube wall 131, an outside wall surface 132, an outside layer 134, an intermediate tie-layer 136, an inside layer 138, and an inside surface 140.

In one embodiment, inner tube wall 118 is formed of a lubricious material to provide a lubricious inside surface 120 offering less resistance when advancing the catheter over a guide wire. In this embodiment, outer tube wall inside surface 140 is formed of the same or compatible lubricious material as inner tube 105. This allows bonding between inner and outer tubes as indicated in region 150. As illustrated in FIG. 4, inner tube 105 and outer tube inner layer 138 are formed of the same material. After heat bonding, the two layers can melt and flow together as indicated by the dashed line between layer 138 and inner tube wall 105. In the example illustrated, bonding only occurs distal of orifice 104 and near orifice 104. In other embodiments, the bonding occurs further distal of orifice 104. Any suitable location for bonding inner to outer tubes is within the scope of the invention. Outer tube 102 has an outside layer 134 formed of a flexible material different from the lubricious material forming inner tube 105. Disposed between outside layer 134 and inside layer 138 is tie-layer 136.

Tie-layer 136, as used herein, refers to a layer which enables or enhances the bonding of the two materials such as the outside and inside layers to one another. The outer outside and inside layers can provide different properties desirable for the catheter. In particular, the outside layer can contribute much of the structural properties of the outer tube, while the inside layer can contribute an inside surface that is bond compatible with the outside surface of the inner tube. The tie-layer is preferably a layer of polymer that is bond compatible with both inside and outside layers. The tie-layer can in turn be formed of more than one layer, but a single layer is preferred to provide a thin tube wall. In some embodiments, the tie-layer enables two materials to bond to one another where such bonding would not occur in the absence of the tie-layer. In other embodiments, the tie-layer enhances bonding, improving the bond strength over that which would otherwise occur. A tie-layer can greatly improve the quality of bonding.

In one embodiment, inner tube 105 is formed of polyethylene, outer tube inside layer 138 is also formed of polyethylene, and outer tube outside layer 134 is formed of a polyether block amide (PEBA) such as PEBAX™. A tie-layer suited for bonding polyethylene and PEBA together such as PLEXAR™ or KRATON™ is used for tie-layer 136 in one embodiment. In some embodiments, a surface treatment can be used to form the tie-layer. In an embodiment having a polyethylene inner tube, the polyethylene provides a lubricious inside tube surface for a guide wire to slide within. In an embodiment having a PEBA outer tube outer layer, the PEBA provides a strong, yet flexible material, having superior flexibility to polyethylene in most catheter applications. The flexibility is of importance in the distal catheter region, which may be required to traverse tortuous secondary and tertiary coronary vessels.

The polyethylene inner tube provides the advantages of a lubricious inner surface, while the tri-layer outer tube provides flexibility imparted by the PEBA outside layer. The polyethylene outer tube inside layer provides a layer compatible for heat bonding with the polyethylene inner tube outside surface. The outer tube tie-layer provides a means for joining the outer tube polyethylene and PEBA layers. Catheter distal region 100 thus has the advantages of a lubricious guide wire lumen and the advantages of a distal catheter outer tube formed of a flexible material.

Referring now to FIG. 5, another embodiment of the invention is illustrated in a catheter distal region 200 including an inner tube 205 disposed within an orifice 204 in an outer tube 202. Outer tube 202 includes a proximal portion 230, a tube wall 231, an outside surface 232, and an inside surface 240. Outer tube 202 and tube wall 231 are formed of a first material extending from outside surface 232 to inside surface 240. Inner tube 205 includes a tube wall 218 having an inside surface 220, an inside layer 221, a tie-layer 225, an outside layer 223, and an outside surface 222. Inner tube inside layer 221 is formed of a second, lubricious material, and outside layer 223 is preferably formed of the first material or a material bond compatible with the first material. Tie-layer 225 provides a bond, holding inside layer 221 and outside layer 223 together. Outer tube inside surface 240 and inner tube outside surface 222 are formed of the same first material, allowing for formation of a good heat bond securing the inner tube within the outer tube. In the bonding region proximate orifice 204, the inner and outer tubes are secured at a distal bonding region 250 disposed distal of orifice 204 and at a proximal bonding region disposed proximal of orifice 204, better visualized by bonding region 851 in FIG. 2, as are other bonding regions disposed proximal of the orifice in figures similar to FIG. 5. Outer tube 202 can be bonded to inner tube 205 using both outer tube inside surface 240 and outside surface 222. In a preferred embodiment, the first material forming outer tube 202 is PEBA, as is the material forming inner tube outside layer 223, while the second material forming inner tube inside layer 221 is polyethylene. The embodiment illustrated thus can have a lubricious polyethylene inside surface for the guide wire lumen and a flexible PEBA outer tube.

Referring now to FIG. 6, a catheter distal region 300 having an interrupted tri-layer outer tube is illustrated. Catheter distal region 300 includes an inner tube 305 disposed within an orifice 304 in an outer tube 302. Inner tube 305 includes a wall 318, an inside surface 320, and an outside surface 322. Outer tube 302 includes a tube wall 331 having an inside surface 340, an outside surface 332, a proximal portion 330, a distal portion 342, and an intermediate portion 337 disposed between the proximal and distal portions. In a preferred embodiment, intermediate portion 337 includes a tie-layer 336 formed as a short layer disposed at an angle relative to the tube wall, such that tie-layer 336 extends over a length indicated at "D1" in FIG. 6. Tie-layer 336, as illustrated, longitudinally separates or interrupts the proximal and distal portions of the layer. In a preferred embodiment, D1 has a length between about one (1) mm and one hundred (100) mm and a width of about one hundred (100) mm. In one method, tie-layer 336 is formed using a Short and Controlled Transition Section (SCTS) extrusion technique, as described in U.S. Pat. No. 5,533,985, issued to Wang, herein incorporated by reference. In one embodiment, inner tube 305 is formed of polyethylene, and outer tube 302 has proximal portion 330 formed of polyethylene, tie-layer 336 formed of PLEXAR™, and distal portion 342 formed of PEBA. In one embodiment, inner tube outside surface 322 is bonded to outer tube inside surface 340, as indicated at 350 and by region 851 in FIG. 2 as discussed previously. In embodiments supporting bonding involving both the inside and outside surface of the outer tube, the bonding region can extend both proximal and distal of orifice 304. Bonding can also extend over the sides of inner tube 305 but is not illustrated in the longitudinal, cross-sectional view of FIG. 6. The embodiment of FIG. 6 thus provides a lubricious inner tube for ease of guide wire movement and an outer tube proximal portion for bonding to the lubricious inner tube, while providing a flexible material forming most of the outer tube.

Referring now to FIG. 7, a catheter distal region 400 having an interrupted tri-layer inner tube is illustrated. Catheter distal region 400 includes an outer tube 402 having an inner tube 405 disposed within an orifice 404 in outer tube 402. Inner tube 405 includes a proximal portion 412, a distal portion 414, and an intermediate portion 413 having a length indicated at "D2". Intermediate portion length D2 is preferably between about one (1) mm and fifty (50) mm. Intermediate portion 413 includes a tie-layer 436 preferably disposed at an angle relative to the inner tube wall. In one method, tie-layer 436 is formed using a Short and Controlled Transition Section (SCTS) extrusion technique previously described. Outer tube 402 and inner tube proximal portion 412 are preferably formed of the same flexible material to allow for improved bonding. Inner tube distal portion 414 is preferably formed of a lubricious material, while tie-layer 436 is preferably formed of a material suitable for adhering the flexible and lubricious materials together. In one embodiment, the inner tube proximal portion 412 is bonded to outer tube 402, as indicated at 450 and by region 851 in FIG. 2. The embodiment illustrated thus provides a lubricious material for most of the length of inner tube 405, while providing a flexible material for outer tube 402. Forming inner tube proximal portion 412 of a bond compatible or identical material to the material of the outer tube allows bonding together of the inner and outer tubes.

Referring now to FIG. 8, a catheter distal region 500 is illustrated having an inner tube 505 inserted into an orifice 504 in an outer tube 502. Inner tube 505 includes a tube wall 518, a proximal portion 512, and a distal portion 514. In proximal portion 512, inner tube wall 518 includes an inner layer 517, which is preferably formed of the same material as the entire tube wall at distal portion 514, a tie-layer 536 disposed over the tube wall or inner layer 517, and an outside layer 534 disposed over the tie-layer. The proximal portion of inner tube 505 thus can have two added outer layers in the proximal portion. In a preferred embodiment, outer tube 502 is formed of a flexible material and inner tube outside layer 534 is formed of the same material, thereby allowing for bond compatibility between inner and outer tubes. In a preferred embodiment, inner tube wall 518 is primarily formed of a lubricious material, and tie-layer 536 is formed of a material able to bond to both the inner lubricious material and the outer flexible material. In the embodiment illustrated, bonding occurs as indicated at 550 and at 851 in FIG. 2. In one embodiment, inner tube proximal portion 512 is formed using SCTS technology previously described. The portion of inner tube having the tie-layer and outside layer can be disposed anywhere on the inner tube where bonding to the outer tube is contemplated. In one embodiment, multiple short tri-layer portions are disposed over the length of the inner tube. In this embodiment, the added two layers are added to an inner tube where needed. The additional two layers over the inner tube preserves the lubricious inner walls of the inner tube while improving the bonding compatibility between the inner and outer tubes. In one embodiment, inner tube inside layer 517 and distal portion 514 are formed of polyethylene, tie-layer 536 is formed of PLEXAR™, and outside layer 534 is formed to of PEBA. The embodiment provides a lubricious lumen wall for guide wire movement and a flexible catheter outer tube.

Referring now to FIG. 9, a catheter distal region 600 is illustrated having a two-layer inner tube 605 disposed within an orifice 604 and in an outer tube 602. Inner tube 605 has a tube wall 618 formed of an inside layer 638 and an outside tie-layer 636. Inner tube inside layer 638 is preferably formed of a lubricious material and outer tube 602 is preferably formed of a flexible material different from the material forming the inner tube inside layer. Bonding between inner and outer tubes is indicated at 650, but the bonding location is varied in different embodiments. In one embodiment, inside layer 638 is formed of polyethylene, tie-layer 636 is formed of PLEXAR™, and outer tube 602 is formed of PEBA. The catheter distal region illustrated in FIG. 9 can have a lubricious inner tube inside wall for guide wire movement and a flexible outer tube wall.

Referring now to FIG. 10, a catheter distal region 700 having a butt-welded proximal portion is illustrated. Catheter distal region 700 includes an inner tube 705 inserted into an orifice 704 and disposed within an outer tube 702. Inner tube 705 includes a proximal portion 712 butt-welded to a distal portion 714. A weld 713 is indicated between the proximal and distal portions. In one embodiment, outer tube 702 is formed of a flexible material and inner tube proximal portion 712 is formed of the same or a bond compatible material. Inner tube distal portion 714 can include a tri-layer tube wall as illustrated, having an inside layer 738, an outside layer 734, and a tie-layer 736 disposed between inside layer 738 and outside layer 734. In a preferred embodiment, outer tube 712 is formed from PEBA, as is inner tube proximal portion 712. In this embodiment, inner tube distal portion 714 includes inside layer 738 formed from polyethylene, where tie-layer 736 can be formed from PLEXAR™ and outside layer 734 can be formed from PEBA. The tri-layer inner tube can provide a lubricious inner surface for guide wire movement, while retaining the flexibility contribution of the PEBA outer layer. In this embodiment, bonding can occur as indicated at 750 and 851 in FIG. 2. The embodiment illustrated thus has a substantial PEBA contribution to flexibility, while providing a lubricious guide wire lumen, as most of the inner tube inside layer can be formed of polyethylene.

FIGS. 4-10 illustrate embodiments of the invention including an orifice through an outer tube wall and an inner tube inserted through the orifice into the outer tube and disposed distal thereof within the outer tube lumen. In another embodiment, a guide wire tube is disposed within an outer tube without being inserted through a wall. In this embodiment, the outside surface of the inner tube is bonded to the inside surface of the outer tube. FIGS. 4-10, and the associated text, illustrate examples of tube construction and materials compatible with this embodiment. In yet another embodiment, a first flexible tube has a second tube having a lubricious inside surface bonded to the first tube outside surface. The second tube can serve as a guide wire tube. In a variation of this embodiment, multiple short, external tubes serve as guide wire tubes. FIGS. 5-10, and the associated text, illustrate examples of tube construction and materials compatible with these external guide wire tube embodiments. In these embodiments, the second guide wire tube outside surface is bonded to the first tube outside surface.

In a preferred method of making the present invention, the first and second tubes are heat bonded together in the bonding region. Other bonding methods can also be used to take advantage of the compatible materials presented for bonding by the present invention. Other bonding methods believed suitable for use with the present invention include sonic welding and solvent welding.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A catheter shaft comprising:
   a first tube including an inflation lumen defined by an inside wall surface in fluid contact with a dilation balloon, an outside wall surface, the first tube having an orifice in a portion of the first tube, the first tube formed of a first material;
   a second tube inserted through the orifice and extending distally from the orifice inside the inflation lumen, the second tube comprising an inner layer, an outer layer and an intervening intermediate layer, the second tube having a length and a lumen therethrough, the inner layer defining an inner wall surface, the outer layer defining an outside wall surface; and
   a bonding region wherein the second tube outside wall surface is bonded to the first tube outside wall surface by re-flow of the first and second tube outside wall surfaces;
   further wherein the second tube outside wall surface is bonded to the first tube inside wall surface by re-flow of the first tube inside wall surface and second tube outside wall surface.

2. The catheter shaft of claim 1, wherein the outer layer of the second tube comprises a material that is bond-compatible with the first tube first material.

3. The catheter shaft of claim 1, wherein the outer layer of the second tube is also formed of the first tube first material.

4. The catheter shaft of claim 1, wherein the intermediate layer of the second tube comprises a material that is bond-compatible with both the inner layer lubricious material and the outer layer material.

5. The catheter shaft of claim 1, wherein the second tube comprises a proximal portion disposed proximally of the first tube orifice and a distal portion disposed distally of the first tube orifice, within the first tube inflation lumen.

6. The catheter shaft of claim 1, wherein the first tube first material comprises a polyether block amide.

7. The catheter shaft of claim 1, wherein the second tube outer layer comprises a polyether block amide.

8. The catheter shaft of claim 1, wherein the second tube inner layer comprises polyethylene.

9. The catheter shaft of claim 1, further comprising a stiffener disposed within the first tube.

10. The catheter shaft of claim 9, wherein the stiffener is disposed within the lumen of the first tube.

11. The catheter shaft of claim 9, wherein the stiffener is disposed within the first tube from a point proximal the proximal end of the second tube to a point distal of the bonding region.

* * * * *